(12) United States Patent
Foley et al.

(10) Patent No.: US 8,758,225 B2
(45) Date of Patent: Jun. 24, 2014

(54) ADAPTER FOR ENDOSCOPES AND RELATED METHOD

(75) Inventors: Brian Foley, Wilbraham, MA (US); William LeBlanc, Indian Orchard, MA (US)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 1241 days.

(21) Appl. No.: 12/181,248

(22) Filed: Jul. 28, 2008

(65) Prior Publication Data

US 2009/0030271 A1    Jan. 29, 2009

Related U.S. Application Data

(60) Provisional application No. 60/962,106, filed on Jul. 26, 2007.

(51) Int. Cl.
*A61B 1/00* (2006.01)
*A61B 1/04* (2006.01)

(52) U.S. Cl.
CPC ......... *A61B 1/00137* (2013.01); *A61B 1/00133* (2013.01); *A61B 1/00121* (2013.01)
USPC .......................................... 600/106; 600/117

(58) Field of Classification Search
CPC ........... A61B 1/00121; A61B 1/00133; A61B 1/00137
USPC ........................... 600/106, 108, 154; 604/171
See application file for complete search history.

(56) References Cited

U.S. PATENT DOCUMENTS

| | | | |
|---|---|---|---|
| 5,549,601 A * | 8/1996 | McIntyre et al. | 606/15 |
| 5,662,616 A * | 9/1997 | Bousquet | 604/175 |
| 6,200,332 B1 | 3/2001 | Del Giglio | |
| 6,695,816 B2 * | 2/2004 | Cassidy, Jr. | 604/165.02 |
| 2007/0106286 A1 | 5/2007 | Harschack et al. | |
| 2007/0270640 A1 * | 11/2007 | Dimitriou et al. | 600/106 |
| 2009/0005767 A1 | 1/2009 | Moran et al. | |

OTHER PUBLICATIONS

International Search Report, Nov. 12, 2008.

* cited by examiner

*Primary Examiner* — Alireza Nia
(74) *Attorney, Agent, or Firm* — Bulesh J. Skutnik; B J Associates

(57) ABSTRACT

An adapter for endoscopic treatments has a fiber constraint device that is set at a desired maximum fiber retraction distance, and provides a physical barrier to prevent excessive fiber retraction into the endoscope. The restricted retraction prevents the fiber from firing within the endoscope, thus avoiding expensive damage to both the endoscope and fiber. This benefits the patient with potentially shorter treatment time and less exposure to anesthesia. The adapter also limits maximum extension of fibers. Limiting maximum extension protects the fiber tip and avoids patient complications. The adapter is securely attached to the optical fiber with a connecting means. When using directionally radiating fiber tips, fiber orientation can be defined and the fiber can be rotated relative to the initial angular position of the fiber tip.

17 Claims, 3 Drawing Sheets

ADAPTER FOR ENDOSCOPES AND RELATED METHOD

CROSS-REFERENCE TO PRIORITY APPLICATION

This application claims priority under 35 U.S.C. §119 to co-pending U.S. Provisional Patent Application Ser. No. 60/962,106 filed Jul. 26, 2007, entitled "Adapter for Endoscopes", which is hereby expressly incorporated by reference as part of the present disclosure.

BACKGROUND OF THE INVENTION

1. Field of the Invention

The present invention relates generally to the field of fiber optic scopes used in procedures intended for precise, invasive functions, such as tissue ablation.

2. Information Disclosure Statement

Treatment of cellular tissues usually requires direct contact of the target tissue with a medical instrument, usually by surgical procedures, exposing both the target and intervening tissue to substantial trauma. Often, precise placement of a treatment probe is difficult because of the location of targeted tissues in the body or the proximity of the target tissue to an easily damaged, critical body organ, nerves or other components.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Optical fibers ("fibers") and lasers have been used to destroy malignant, benign and other types of cells and tissues from a wide variety of anatomic sites and organs. This method involves introducing an endoscope to an area adjacent to the tissue to be treated. The fiber is then passed through the endoscope to the treatment zone and radiant energy is applied to the targeted tissue. The fiber can be positioned using a fiber optic viewing system incorporated within the endoscope. Separate components may be included in the system to flush the tissue with fluid.

One example of endoscopic treatment with an optical fiber involves using a side fire optical fiber tip ("side fire") for use in high power laser applications, as disclosed in U.S. Pub. No. US 2007/0106286 A1, Harschack et al. Side firing directs radiant energy to a treatment area lateral to the endoscope's and fiber's longitudinal axis. One specific application of side fire endoscopic treatment includes treating isolated masses in the prostate gland, for example. The endoscope provides the side fire access to the prostatic mass and radiant energy is directed towards the gland, through walls of the urethra, into the surrounding prostate cells, in an effort to ablate the tissue constricting the urethra.

Endoscopic fiber treatments have complications, however. Once the endoscope and fiber are in position to treat the targeted tissue, the user must be careful and avoid retracting the fiber tip into the endoscope. Excessive retraction allows the fiber to fire inside the endoscope creating several complications. The fiber may blast the endoscope for example, causing expensive or irreparable damage. In addition, reflected radiation can cause self-inflicted damage to the fiber tip, requiring repair or replacement. If damage to the endoscope or fiber tip occurs during a treatment procedure, efficacy is compromised. Damage to either component requires replacement, subjecting the patient to an extended treatment time and increased exposure to anesthesia.

Problems may also occur with excessive fiber extension. Excessive extension may force the fiber tip against body tissue causing it to break. Breakage may once again extend patient treatment time and exposure to anesthesia, if replacement is necessary. In addition, the severed fiber portion may have to be removed from the patient.

The prior art in this field involves the user holding the fiber or a simple handle to manipulate the fiber's position. The user generally tracks the fiber tip's position using a fiber optic viewing system. Beyond viewing the fiber's position, nothing prevents the user from retracting the fiber tip into the endoscope or forcing the fiber tip into tissue.

A precise invasive fiber optic treatment method is disclosed in U.S. Pat. No. 6,200,332 by Del Giglio. The disclosed method involves an optical fiber inserted into a desired treatment area with a needle and fixed hand piece. The user monitors the fiber position visually, typically with the aid of an aiming beam. Positioning of the fiber tip is aided with a notch in the hand piece that remains a fixed distance from the fiber tip. This notch also indicates fiber tip orientation because it remains fixed relative to the direction of the fiber tip. Once in position, the user retracts the needle that delivered the fiber to the treatment site. The retracted needle remains a fixed distance behind the fiber tip. This method requires a dedicated hand piece, introducing needle and a single stroke before moving to another treatment site. It does not address treatments where repeated bursts and movement back and forth along the fiber's axis are required during a single treatment. More significant is the dedicated nature of the device to specific treatments. Further, the device is not adapted for use with an endoscope and cannot itself act as one.

It is an object of the present invention to overcome one or more of the above-described drawbacks and/or disadvantages of the prior art.

SUMMARY OF THE INVENTION

Briefly stated, the present invention provides a scope adapter and related method to increase fiber optic medical probe efficiency and efficacy during endoscopic and other treatments. This device is an adaptable module that prevents scope and fiber damage, and may increase treatment efficacy. The adapter has a fiber constraint device, which is set at a desired maximum retraction distance, providing a physical barrier to prevent excessive fiber retraction into the scope. The restricted retraction may be set to prevent the fiber from firing within the scope, thus avoiding expensive damage to both the scope and fiber. This benefits the patient with potentially shorter treatment time and less exposure to anesthesia. The adapter also limits maximum extension of fibers. Limiting maximum extension protects the fiber tip and avoids patient complications. The adapter is securely attached to the optical fiber with a connecting means, which is the adapter's most proximal component. When dealing with directionally radiating fiber tips, fiber orientation can be defined, and rotation during treatment of the fiber probe relative to the fiber tip's initial position is possible.

One advantage of the present invention is that the adapter and method improve on the state of the art by preventing excessive fiber retraction into the scope, preventing excessive fiber extension into the patient, protecting the scope and fiber tip from damage, and/or increasing patient safety and treatment efficacy.

Another advantage of the present invention is that the adapter and method physically limit the fiber slide range with maximum extended and retracted positions and, in turn, facilitate in preventing human error in fiber optic treatments.

Another advantage of the currently preferred embodiments of the present invention is that they can prevent the fiber of an endoscopic or other optical fiber treatment system from damaging either itself or the scope.

Another advantage of the currently preferred embodiments of the present invention is that they can increase the precision of the fiber tip position and orientation in endoscopic or other fiber optic treatment systems.

Another advantage of the currently preferred embodiments of the present invention is that they can increase patient safety and treatment efficacy when treated with an endoscopic or other optical fiber treatment system.

Yet another advantage of the currently preferred embodiments of the present invention is that they can provide a nearly universal adapter capable of being used with any of numerous types of scopes or hand pieces, such as any of numerous different types of endoscopes.

The above, and other objects, features and advantages of the present invention, and/or of the currently preferred embodiments thereof, will become apparent from the following description read in conjunction with the accompanying drawings, wherein like reference numerals are used to indicate like elements throughout the various figures.

DETAILED DESCRIPTION OF PREFERRED EMBODIMENTS

The present invention is directed to a new device in the form of an adapter for a scope used in endoscopic or other fiber optic medical treatments. The term "scope" is used herein to mean any of numerous different devices that are currently known, or that later become known, for introducing a waveguide, such as a fiber optic, into an anatomical structure, such as within a human body, and includes without limitation any of numerous different endoscopes and hand pieces for introducing and/or manipulating fiber optics. In one embodiment, the adapter includes a set of at least three tubes designed to accept an optical fiber and direct it into the operating channel of a scope. The adapter has a first or proximal tube, a second or central tube, and a third or distal tube. In another embodiment, the adapter includes a set of at least two tubes, including a first or proximal tube and a second or central tube. The adapter provides a useful advantage in many invasive procedures wherein an optical fiber is used with a scope, such as an endoscope.

Figure 1:
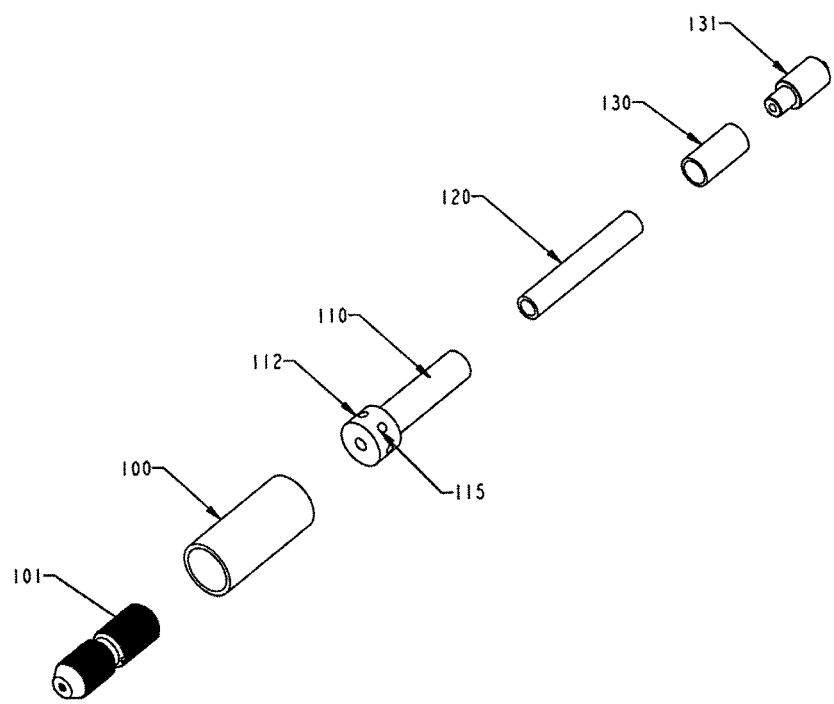
FIG. 1 is a perspective, exploded view of an embodiment of an adapter of the present invention having three tubes.

As shown in FIG. 1, the adapter includes a fiber locking means 101 that receives therethrough a fiber optic or other waveguide (not shown). A proximal tube 100 is slidably received over the distal end of a central tube 110, and the proximal end of the proximal tube 100 is fixedly secured to the fiber locking means 101. The central tube 110 defines on its proximal end a step up portion 112 that is slidably received within the proximal tube 100. The proximal tube 100 includes on its distal end a receiver ring (not shown) that releasably engages the step up portion 112 to releasably retain or lock the step up portion, and thus the adapter in a fully retracted position, and that also defines a distal stop surface to retain the step up portion within the proximal tube. Accordingly, the step up portion 112 of the central tube 110 is slidable between the distal end of the proximal tube 100 defining the fully retracted position of the adapter and fiber, and the proximal end of the proximal tube 100 defining the fully extended position of the adapter and fiber. The distal end of the central tube 110 is fixedly secured to a central tube flexible means 120 that is, in turn, fixedly secured on its distal end to a distal tube 130. The distal tube 130 is fixedly secured between the central tube flexible means 120 and a scope locking means 131. The scope locking means 131 is connectable to the proximal end of a scope, such as an endoscope (not shown), to attach the adapter to the scope.

The proximal tube 100 accepts the optical fiber or other waveguide connected or connectable to a laser source (not shown) and secures the fiber into place with the fiber locking means 101. The fiber optic is received through the adapter and into the scope, such as an endoscope. As described further below, the fiber locking means 101 fixedly secures the fiber optic to the adapter, and the adapter is movable between fully extended and fully retracted positions to thereby limit both the degree to which the fiber tip may be extended through the distal end of the scope, and the degree to which the fiber tip may be retracted relative to, or within the distal end of the scope. The proximal tube 100 is slidably mounted over the central tube 110 and is movable between (i) the fully retracted position in which the retainer ring within the distal end of the proximal tube 100 releasably engages the step up portion 112 of the central tube 110, and (ii) the fully extended position in which the step up portion 112 of the central tube 110 is located at the proximal end of the proximal tube 100 and engages the fiber locking means 101 or other stop surface formed at the proximal end of the proximal tube. Accordingly, the total range of movement for the fiber tip is defined as the axial distance or length between the distal end of the step up portion 112 and the proximal end of the central tube flexible means 120 connected to the central tube 110.

The step up portion 112 is provided with a locking mechanism 115 that releasably engages the receiver ring (not shown) within the distal end of the proximal tube 100 to releasably retain the adapter, and thus a fiber secured to the adapter, in a fully retracted position. One advantage of the locking mechanism 115 is that the adapter can be releasably retained in the fully retracted position during, for example, loading of the fiber into the adapter in order to stabilize the position of the adapter during loading, and precisely load and position the fiber within the adapter and scope. In the illustrated embodiment, during loading of the fiber, the adapter is releasably retained by the locking mechanism 115 in the fully retracted position, and thus the fiber is loaded into the adapter and scope and the fiber tip is positioned at a predetermined or other desired position of maximum retraction relative to the distal end of the scope. In some embodiments of the present invention, the fully retracted position is set so that the fiber tip is never received within the tip of the scope to prevent damage to the scope and/or fiber. Then, the fiber locking means 101 is actuated to fixedly secure the fiber to the adapter, and thus fix both the degree to which the fiber tip may be fully extended and retracted relative to the distal tip of the scope. Once the fiber is loaded, the user can apply sufficient axial pressure by pushing inwardly or distally on the fiber and/or adapter to release the locking mechanism 115 from the receiver of the proximal tube 100 and, in turn, allow the adapter and fiber secured thereto to be freely moved between the fully retracted and extended positions.

In the illustrated embodiment, the locking mechanism 115 is a detent locking mechanism that includes a plurality of protuberances, such as balls, that are angularly spaced relative to each other on the step up portion 112, and that are releasably retained within a corresponding groove formed in the receiver of the proximal tube 100 to releasably retain or lock the position of the adapter. In another embodiment, the step up portion 112 includes an o-ring or like resilient member that is received within a corresponding groove formed in the receiver of the proximal tube 100 to releasably retain or lock the adapter. In another embodiment, the step up portion includes a c-clip or like device forming a raised locking surface on the step up portion 112 that is received within a groove or other recessed surface on the proximal tube 100 to releasably lock the two components and thus the position of the adapter. As may be recognized by those of ordinary skill in the pertinent art based on the teachings herein, the locking mechanism may take the form of any of numerous different locking mechanisms that are currently known, or that later become known, and may be positioned on the adapter to releasably lock the adapter in the fully retracted, fully extended (e.g., by positioning the receiver ring on the proximal end of the proximal tube), or other desired position.

In the illustrated embodiment, the central tube flexible means 120 is defined by a flexible tube, such as a flexible plastic tube. In some embodiments, the central flexible tube means 120 is defined by a tube including a portion oriented at an acute angle relative to an elongated axis of the adapter and/or of the endoscope to, in turn, allow the proximal end of the adapter to be laterally spaced relative to the axis of the endoscope or other type of scope to which the adapter is attached. In some such embodiments, the angle of the flexible tube means is within the range of about 5° to about 45°. If desired, the element 120 need not be flexible, but rather may be rigid, particularly in the event this component is angled or includes an angled portion.

In one embodiment of the present invention, the central flexible tube 120 is adhesively bonded or glued to the central tube 10 and distal tube 130, and the proximal tube 100 is adhesively bonded or glued to the fiber locking means 101. However, as may be recognized by those of ordinary skill in the pertinent art based on the teachings herein, these components, and/or other components of adapter, may be secured or otherwise connected to one another in accordance with any of numerous different mechanisms that are currently known, or that later become known, including without limitation, by bonding, gluing, welding, or by mechanical connection, such as with threads or other fasteners.

In some embodiments of the present invention, the adapter further includes a rotation limiter of a type known to those of ordinary skill in the pertinent art (not shown) that is incorporated into the proximal tube 100 and/or the central tube 110 to limit the degree to which the fiber may be rotated to, for example, prevent damage to the scope. In one such embodiment, the proximal tube 100 and/or the central tube 110 includes angularly spaced stop surfaces that are angularly spaced relative to each other to define the degree to which the proximal tube may be rotated relative to the central tube (or vice versa), and thus the degree to which the fiber secured to the proximal tube may be rotated relative to the scope. One advantage of this feature is that it can be employed to prevent a side firing fiber from being rotated into a position that would allow the fiber to fire into the scope and damage the scope. Another advantage of this feature is that it can control the limit to which a side firing fiber can be rotated during a treatment within an anatomical structure. For example, during a fat removal procedure it is desirable to fire the fiber toward the fat on one side of the scope and not toward the skin on another side of the scope. In these procedures, the rotation limiter can prevent the fiber from being fired toward the skin. Yet another advantage of this feature is that the scope may define a lateral opening for a side firing fiber, and the rotation limiter can allow the fiber to be angularly positioned or rotated only within the angular extent of the lateral opening to thereby prevent the fiber from being fired into the scope and damaging the scope and/or fiber.

The most distal part of distal tube 130 is defined by the scope locking means 131. The scope locking means 131 securely fixes the adapter to a scope, such as an endoscope, and is highly adaptable in order to allow the adapter to be used on many different types of scopes. In one embodiment, the scope locking means 131 is a luer lock. In another embodiment, the scope locking means 131 is a threaded fitting. In yet another embodiment, the scope locking means 131 is a compression fitting. In alternative preferred embodiments, other types of fittings that are currently known or that later become known may be used to form the scope locking means 131. The illustrated embodiment of the fiber locking means 101 is a compression fitting, but any of numerous other waveguide connectors that are currently known, or that later become known, equally may be employed. Accordingly, as may be recognized by those of ordinary skill in the pertinent art based on the teachings herein, the components of the adapter may take the form of any of numerous different components that are currently known, or that later become known, for performing the functions of the respective components described herein.

Figure 1A:
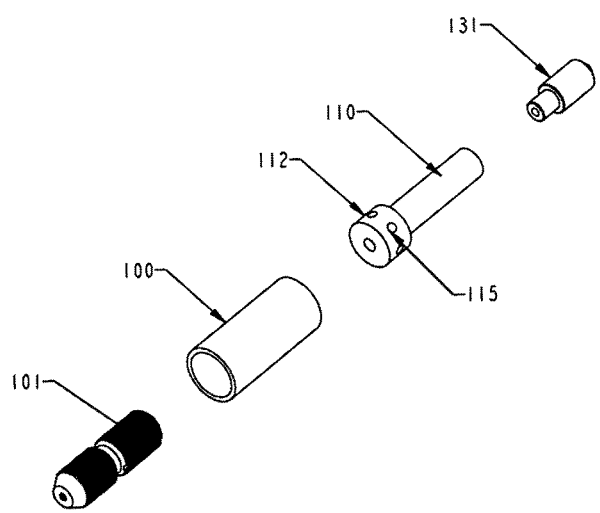
FIG. 1A is a perspective, exploded view of another embodiment of an adapter of the present invention having two tubes.

FIG. 1A shows the adapter components of a two tube embodiment. In this embodiment, the distal tube 130 and the central tube flexible means 120 are omitted. The central tube 110 extends to the endoscope locking means 131.

Figure 2A:
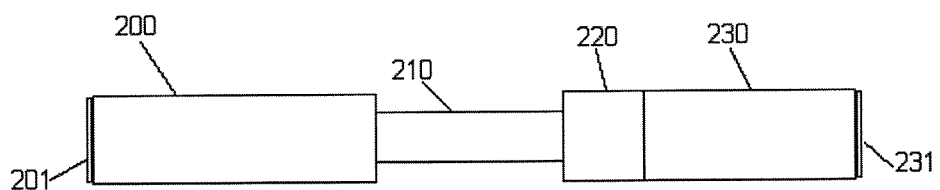
FIG. 2A is a side elevational view of an embodiment of an adapter of the present invention in a fully retracted state wherein the distal fiber tip is closest to the endoscope.

FIG. 2A shows a preferred embodiment of the adapter in the fully retracted position. In this position, the proximal tube 200 is at the maximum distance away from the distal tube 230 and the fiber tip is closest to the endoscope. In this embodiment, the fiber locking means 201 secures the fiber to prevent the fiber tip from retracting into the endoscope.

Figure 2B:
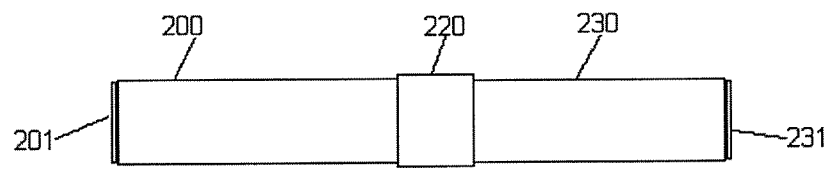
FIG. 2B is a side elevational view of another embodiment of an adapter of the present invention in a fully extended state wherein the distal fiber tip is spaced furthest from the endoscope within the patient's body during normal operation.

FIG. 2B shows another preferred embodiment of the adapter in the fully extended position. As can be seen, the proximal tube 200 is at the minimal distance away from the distal tube 230. The central tube flexible means 220 prevents the proximal tube 200 from moving any closer to the distal tube 230 due to the fact that the central tube flexible means 220 defines a fixed axial distance or minimum space between the distal end of the central tube flexible means 220 and the proximal end of the distal tube 230. In this position, the fiber tip is extended as far out of the scope as possible. In alternative preferred embodiments, the central tube flexible means 220 is replaced with other means to join the central tube 210 (see FIG. 2A) and the distal tube 230. For example, a connecting mechanism that is solid rather than tubular, or that is substantially rigid, as opposed to flexible, may be employed. The central tube 210 in FIG. 2A defines a fixed, predetermined extension range, that may be, for example, within the range of about ¼ to about 1¼ inch, and more preferably within the range of about ½ to about 1 inch. If desired, a plurality of adapters defining different extension ranges may be provided, and the appropriate adapter (or extension range) may be selected based on the procedure or user preference.

The present invention is further illustrated by the following examples, but is not limited thereby:

EXAMPLE 1

A modified fiber with two radial lines can be used with the present invention. The radial lines indicate to the user that the fiber tip has cleared the endoscope and is safe to fire. The practitioner first secures the adapter to the endoscope with the endoscope locking means. The endoscope is then positioned within the patient. The adapter is now in its fully retracted position as shown, for example, in FIG. 2A. The fiber is passed through the adapter and endoscope. The fiber locking mechanism, which in this exemplary embodiment may be a squeeze lock type connector, is tightened when the second radial line is seen through a fiber optic viewing system. This technique prevents the fiber tip from retracting into the endoscope and damaging the endoscope or fiber. Optionally, a notch or indicator may be provided on the adapter, which aligns with the region from which the fiber is fired, to facilitate the ability of a user to orient the position of the firing fiber.

EXAMPLE 2

To treat benign prostatic hyperplasia ("BPH"), a high powered laser with a side fire optical fiber tip is used with the adapter of the present invention. The adapter's ability to limit extension and retraction increases the patient's chance of an effective, timely and safe procedure. The laser, fiber and related system, and the method of treating BPH, may be the same or substantially similar to that disclosed in commonly-assigned U.S. patent application Ser. No. 12/123,114, filed May 19, 2008, entitled "DEVICE AND METHOD FOR BENIGN PROSTATIC HYPERPLASIA LASER TREATMENT", which is hereby expressly incorporated by reference as part of the present disclosure.

EXAMPLE 3

Using a threaded central tube 210 and correspondingly threaded distal tube 230, the central tube flexible means 220 may be omitted. In this embodiment, the central tube 210, as shown in FIG. 2A, defines an axial length of about ½ inch. Accordingly, in this embodiment, the distance between full extension and retraction is fixed at about ½ inch.

EXAMPLE 4

The endoscope locking means is a luer lock to firmly secure the adapter to the endoscope. This provides a commonly used fitting that supplies the necessary rigidity between the adapter and an endoscope.

EXAMPLE 5

In this embodiment the adapter is provided with a solid, angled central tube means 120 (see FIG. 1), i.e., a piece that is solid, relatively rigid, and is oriented at an angle, such as an acute angle relative to the elongated axis of the adapter and/or scope. The angled connector 120 is designed to provide greater clearance for the adapter if a camera and/or other viewing device or accessory is used with the endoscope. The angled tube or connector allows plural endoscope accessories to be simultaneously used in close proximity.

EXAMPLE 6

In this embodiment the adapter is provided with a flexible central tube means 120 (see FIG. 1). The flexible tube means 120 in the adapter provides bending flexibility to the adapter at the distal end of the adapter where the distal tube and endoscope are attached. As may be recognized by those of ordinary skill in the pertinent art based on the teachings herein, other devices or mechanisms that are currently known, or that later become known, for flexibly connecting the tubes or other components of the adapter equally may be employed, including, for example, a non-tubular flexible connector.

EXAMPLE 7

In addition to the side firing tip on the fiber optic probe, other fiber probe ends can benefit from the scope adapters of the present invention. Using the adapter on an endoscope with a high powered laser with a straight fire optical tip provides the same protection to the endoscope, fiber and patient as described above.

EXAMPLE 8

Even absent the risk of endoscope or fiber damage, the adapter helps to maintain treatment efficacy. Lower powered laser applications, for example, using the adapter with a diffuser tip, benefit from the adapter. If such a fiber is unknowingly retracted within the endoscope, the tissue does not receive the exposure to the radiation. Preventing excessive fiber retraction, therefore, can benefit the patient by providing precise radiation treatment.

Having described several preferred embodiments of the invention with reference to the accompanying drawings, it is to be understood that the invention is not limited to these precise embodiments, and that various changes and modifications may be effected therein by those skilled in the art without departing from the scope or spirit of the invention as defined in the appended claims. For example, the components of the adapter may take the form of any of numerous different components that are currently known, or that later become known, for performing the functions of the respective components as described herein. In addition, the components may be formed of any of numerous different materials, in any of numerous different shapes, sizes and/or configurations, and may be used with any of numerous different fibers or other waveguides, and/or with any of numerous different scopes, that are currently known, or that later become known. In addition, the adapters of the present invention may include more, fewer and/or different components than those described above. Accordingly, this detailed description of the currently preferred embodiments is to be taken in an illustrative as opposed to a limiting sense.

What is claimed is:

1. An adapter for regulating movement of a waveguide relative to a scope, comprising:
   a first connector for connecting the adapter to a scope;
   a second connector for connecting the adapter to the waveguide;
   wherein at least one of the first and second connectors is movable relative to the other between (i) an extended position wherein a distal tip of the waveguide is extended relative to the scope, and (ii) a retracted position wherein the distal tip of the waveguide is retracted relative to the scope;
   a first member fixedly coupled to the first connector;

and a second member coupled securely to the second connector, wherein at least one of the first and second members is movable relative to the other between the extended and retracted positions:
wherein the first member includes a stop component axially spaced relative to the first connector that engages the second member in the retracted position and defines a range of movement between the extended and retracted positions: wherein the stop component protrudes from other sections of the first member:
wherein the second member is a tubular member; and wherein an inner surface of the second member is slidably mounted over an outer surface of the stop component; and
wherein the first connector is coupled to the second connector by a flexible connector that provides the adapter bending flexibility relative to an elongated axis of the scope; and
wherein the flexible connector is coupled between the first member and first connector.

2. An adapter as defined in claim 1, wherein in the extended position the distal tip of the waveguide is extended a maximum distance outwardly relative to a distal tip of the scope, and in the retracted position the distal tip of the waveguide is either retracted a maximum distance inwardly within the distal tip of the scope or is extended a minimum distance outwardly relative to the distal tip of the scope.

3. An adapter as defined in claim 1, further comprising a fourth connector coupled between the flexible connector and the first connector.

4. An adapter as defined in claim 3, wherein at least one of the flexible connector and the fourth connector is a tubular member.

5. An adapter as defined in claim 1, wherein the flexible connector includes at least a portion thereof oriented at an acute angle relative to an elongated axis of the scope to provide clearance for the adapter.

6. An adapter as defined in claim 1, wherein the first member further includes a locking mechanism that releasably retains the adapter in one of the retracted and extended positions to facilitate loading the waveguide into a correct position within the adapter.

7. An adapter as defined in claim 1, in combination with an endoscope connected to the first connector.

8. An apparatus as defined in claim 7, in further combination with a radiation source, and an optical fiber optically coupled on one end to the radiation source, and connected to the second connector on approximately another end thereof.

9. An adapter as defined in claim 1, further comprising a plurality of tubes coupled between the first and second connectors, wherein at least one tube is axially movable relative to another tube between the extended and retracted positions.

10. An adapter as defined in claim 9, wherein the plurality of tubes includes a proximal tube, a distal tube, and at least one central tube coupled between the proximal and distal tubes.

11. An adapter as defined in claim 1, wherein the distance between the extended and retracted positions is within the range of about ½ inch to about 1 inch.

12. An adapter as defined in claim 1, wherein the first connector is one of a luer lock, a threaded fitting, or a compression fitting.

13. An adapter as defined in claim 1, wherein the second connector is a squeeze lock connector.

14. A method for regulating movement of a waveguide relative to a scope, comprising:
(i) providing the adapter of claim 1;
(ii) connecting the adapter to a proximal portion of the scope;
(iii) introducing the waveguide through the adapter and scope;
(iv) positioning a distal tip of the waveguide relative to a distal tip of the scope;
(v) connecting the adapter to the waveguide with the distal tip of the waveguide approximately in the position of step (iv); and
(vi) limiting with the adapter the degree to which the distal tip of the waveguide is extended from the distal tip of the scope to a fully extended position, and the degree to which the distal tip of the waveguide is retracted relative to the distal tip of the scope to a fully retracted position.

15. A method as defined in claim 14, further comprising the steps of positioning the distal tip of the waveguide at a fully retracted position relative to a distal tip of the scope, and connecting the adapter to the waveguide with the distal tip of the waveguide in the fully retracted position.

16. A method as defined in claim 14, further comprising one of: (i) using the waveguide to remove hyperplasic tissue from a treatment site, (ii) using the waveguide to close or shrink a blood vessel, and (iii) using the waveguide to apply photodynamic therapy to a treatment site.

17. A method as defined in claim 14, further comprising the step of limiting with the adapter the degree to which the waveguide may be angularly rotated about an elongated axis of the scope.

* * * * *